United States Patent [19]

Croco

[11] Patent Number: 5,242,795
[45] Date of Patent: Sep. 7, 1993

[54] TCL-5 GENE REARRANGEMENT INVOLVED IN T-CELL LEUKEMIA AND MELANOMA

[75] Inventor: Carle M. Croco, Philadelphia, Pa.

[73] Assignee: Temple University, Philadelphia, Pa.

[21] Appl. No.: 672,160

[22] Filed: Mar. 20, 1991

Related U.S. Application Data

[63] Continuation of Ser. No. 374,864, Jul. 3, 1989, abandoned.

[51] Int. Cl.$^5$ .................. C12Q 1/68; C12P 19/34; C07H 15/12
[52] U.S. Cl. ........................ 435/6; 435/91.2; 536/23.1; 935/77; 935/78
[58] Field of Search .............. 435/6, 91; 536/26-29, 536/23.1; 436/501; 935/77, 78

[56] References Cited

PUBLICATIONS

Lee et al., Science 237:175-178 (Jul. 10, 1987).
Finger et al., Science 234:982-985 (Nov. 21, 1986).
Gilbert et al., "Abnormalities of Chromosome 1p in Human Neuroblastoma Tumors and Cell Lines," Cancer Genet. Cytogenet., 1982, 7:33-42.
Hershfield, et al., "Conversion of a Stem Cell Leukemia from a T-lymphoid to a Myeloid Phenotype Induced by the Adenosine Deaminase Inhibitor 2'-deoxycoformycin," Proc. Natl. Acad. Sci. USA, 1984, 81:253-257.
Croce, et al., "Gene for alpha-chain of Human T-Cell Receptor: Location on Chromosome 14 Region Involved in T-Cell Neoplasms," Sci., 1985, 227:1044-1047.
Kurtzberg, et al., "Establishment of the DU.528 Human Lymphohemmopoietic Stem Cell Line," J. Exp. Med., 1985, 162:1561-1578.
Balaban, et al., "Karyotypic Evolution in Human Malignant Melanoma," Cancer Genet. Cytogenet., 1986, 19:113-122.
Raimondi, et al., "7q32-q36 Translocations in Childhood T-Cell Leukemia: Cytogenetic Evidence for Involvement of the T-Cell Receptor beta-Chain Gene," Blood, 1987, 69:131-134.
Rabbits, et al., "Chromosomal Abnormalities in Lymphoid Tumours: Mechanism and Role in Tumour Pathogenesis," Trends Genet., 1988, 4:300-304.
Haluska, et al., "Localization of the Human JUN Protooncogene to Chromosome Region 1p31-32," Proc. Natl. Acad. Sci. USA, 1988, 85:2215-2218.
Isobe, et al., "Cloning of the Gene Encoding the beta subunit of the Human T-Cell Receptor Reveals its Physical Organization within the alpha-subunit Locus and its Involvement in Chromosome Translocations in T-Cell Malignancy," Proc. Natl. Acad. Sci. USA, 1988, 85:3933-3937.
Begley, et al., "Chromosomal Translocation in a Human Leukemic Stem-Cell Line Disrupts the T-Cell Antigen Receptor beta-Chain Diversity Region and Results in a Previously Unreported Fusion Transcript," Proc. Natl. Acad. Sci. USA, 1989, 86:2031-2035.
Bale, et al., "Mapping the Gene of Hereditary Cutaneous Malignant Melanoma-Dysplastic Nevus to Chromosome 1p," N. Eng. J. Med., 1989, 320:1367-1372.

Primary Examiner—Stephanie W. Zitomer
Attorney, Agent, or Firm—Banner, Birch, McKie & Beckett

[57] ABSTRACT

A gene is described which is involved in the neoplastic process of a number of different cancers. The gene, termed TCL-5, is located at chromosome 1, band 32, adjacent to the chromosome junction formed during a t(1;14)(p32;q11) translocation. Probes and primers for detecting TCL-5 rearrangements are provided, as well as methods for detecting abnormalities in TCL-5 expression.

28 Claims, 9 Drawing Sheets

```
ch.1     ACCATGTCTGCAGCCCTGAGAAAGCCCTGTCGGGCTTTGTGTGAAGG
         ||||||||||||||||||||||||||
ch.1p⁺   ACCATGTCTGCAGCCCTGAGTTGCTGGGGGATACGCACAGTGCTACA
                             |||||||||||||||||||||||||||
ch.14  5'TGTAAAGCTCTGTAGCACTGTGACTGGGGGATACGCACAGTGCTACA3'
                        D δ₂ ch.1     GACCATGTCTGCAGCCCTGAGAAAGCCCTGTCGGGCTTTGTGTGAA
                            |||||||||||||||||||||||||||||||
ch.14q⁻  TTTCATTGTGCCTTCCTAAGGGAAGCCCTGTCGGGCTTTGTGTGAA
         ||||||||||||||||||||
ch.14  5'TTTCATTGTGCCTTCCTACCACACAGGTTGGAGTGCATTAAGCCTT3'
                        D δ₁
```

```
ch.1      ACCATGTCTGCAGCCCCTGAGAAAGCCCCTGTCGGGCTTTGTGTGAAGG
          ||||||||||||||||||||||||||||||||||||||||||
ch.1p⁺    ACCATGTCTGCAGCCCCTGAGTTGCTGGGGGATACGCACAGTGCTACA
                                ||||||||||||||||||||||||||
ch.14  5'TGTAAAGCTCTGTAGCACTGTGACTGGGGGATACGCACAGTGCTACA 3'
                         ─────────              ──────────
                                    Dδ₂
```

FIG. 5B

```
ch.1      GACCATGTCTGCAGCCCCTGAGAAAGCCCCTGTCGGGCTTTGTGTGAA
          ||||||||||||||||||||||||||||||||||
ch.14q⁻   TTTCATTGTGCCTTCCTAAGGGAAGCCCTGTCGGGCTTTGTGTGAA
          ||||||||||||||||||||||
ch.14  5'TTTCATTGTGCCTTCCTACCACACAGGTTGGAGTGCATTAAGCCTT 3'
          ──────────              ────────────────
                                    Dδ₁
```

TCL-5 GENE REARRANGEMENT INVOLVED IN T-CELL LEUKEMIA AND MELANOMA

The U.S. Government has a paid-up license in this invention and the right in limited circumstances to require the patent owner to license others on reasonable terms as provided for by the terms of grant nos. CA 09485, CA 39860, CA 25875 from the National Institutes of Health.

This application is a continuation of application Ser. No. 07/374,864, filed Jul. 3, 1989.

TECHNICAL FIELD OF THE INVENTION

The invention relates to the area of cancer diagnostics and monitoring. More particularly it relates to the diagnosis and monitoring of cancers associated with chromosomal translocations t(1;14)(p32;q11).

BACKGROUND OF THE INVENTION

A large proportion of leukemias and lymphomas of the B- and T-lymphocyte lineages carry characteristic chromosomal abnormalities (Yunis, (1983), Science 221:227-235). The finding of consistent chromosomal translocations directly involving the MYC and ABL oncogenes in, respectively, Burkitt's lymphoma and chronic myeloid leukemia (see Croce and Nowell, (1985), Blood 65:1-7; Kurzrock et al., (1988), N. Eng. J. Med. 319:990-998, for reviews) led to the hypothesis that chromosomal aberrations that alter the expression of specific genes are involved in the pathogenesis of human leukemias and lymphomas. In T-cell tumors, the majority of chromosomal abnormalities involve the T-cell receptor alpha/delta locus on chromosome 14 at band q11 (Croce et al., (1985), Science 227:1044-1047; reviewed in Rabbitts et al., (1988), Trends Genet. 4:300-304). The direct involvement of this T-cell receptor locus in t(8;14)(q24;q11), t(10;14)(q24;q11), t(11;14)(p13;q11), t(11;14)(p15;q11) and t(14;14)(q11;q32) translocations observed in acute T-cell leukemias has been demonstrated by molecular analysis of the breakpoints involved in these translocations (Finger et al., (1986), Science 234:982-985; Kagan et al., (1987), Proc. Natl. Acad. Sci., USA, 84:4543-4546; Kagan, et al., (1989), Proc. Natl. Acad. Sci., USA, in press; Boehm et al., (1988) EMBO J. 7:385-394; Boehm et al., (1988), EMBO J. 7:2011-2017; Mengel-Gaw et al., (1988), Proc. Natl. Acad. Sci. USA 85:9171-9175; Russo et al., (1988), Proc. Natl. Acad. Sci., USA 86:602-606). Human chromosome 1 band p32 aberrations have been detected in acute T-cell leukemia (Mathieu-Mahul et al., (1986), T.C.R. Acad. Sci. 302:525-528; Raimondi et al., (1987) Blood, 69:131-134, human cutaneous malignant melanomas (Balaban et al., (1986) Cancer Genet. Cytogenet. 19:113-122) and human neuroblastomas (Gilbert et al., (1982) Cancer Genet. Cytogenet., 7:33-42). However prior to the present invention the oncogene or oncogenes involved in these diseases had not been identified nor the chromosomal breakpoints located. Thus the only way to identify these aberrations is by cytogenetics, which is costly and technically difficult.

Thus there is a need in the art for molecular methods of identifying certain chromosomal abnormalities involving human chromosome 1 band p32 so that diagnosis and therapy of the diseases associated with the abnormalities can be performed routinely and inexpensively.

SUMMARY OF THE INVENTION

It is an object of the invention to provide a method of diagnosing or assessing a neoplasm in a human.

It is another object of the invention to provide nucleic acid probes for diagnosing or assessing a neoplasm.

It is yet another object of the invention to provide nucleic acid primers for amplifying translocation junctions resulting from t(1;14)(p32;q11) translocations.

These and other objects of the invention are provided by one or more of the embodiments described below. In one embodiment of the invention a method of diagnosing or assessing a neoplasm in a human is provided comprising isolating DNA of a human from cells suspected of being neoplastic; determining whether a TCL-5 gene on said DNA has been rearranged, a rearranged TCL-5 gene indicating a neoplasm.

In another embodiment of the invention a method of diagnosing or assessing a neoplasm in a human is provided comprising isolating from the human test cells suspected of being neoplastic; determining quantity of expression products of TCL-5 genes in said test cells; comparing the quantity of TCL-5 gene expression products in said test cells with the quantity in control cells, said control cells isolated from healthy cells of the human or from a healthy human, an altered quantity of TCL-5 gene expression products in said test cells relative to said control cells indicating a neoplasm.

In yet another embodiment of the invention a nucleic acid probe is provided which is derived from chromosome 1 sequences located between a translocation junction of a 1p+ chromosome of a t(1;14)(p32;q11) translocation and a restriction enzyme site, wherein there are no other sites for said enzyme between said site and the translocation junction.

In still another embodiment of the invention a pair of nucleic acid primers are provided for amplifying translocation junctions of a 1p+ chromosome of a t(1;14)(p32;q11) translocation wherein one primer of the pair is derived from chromosome 1 sequences and one primer is derived from chromosome 14 sequences.

The present invention thus provides the art with methods, probes and primers for diagnosis and monitoring certain neoplasms which render such diagnosis and monitoring routine and inexpensive.

BRIEF DESCRIPTION OF THE DRAWINGS

FIG. 2 shows analysis of the t(1;14) chromosomal breakpoint on the 1p+ chromosome in leukemic cell lines. Panel A shows hydridization of DNA from t(1;14) cell lines with the TCR and pJK3.OS probe. DNA (10 ug) was isolated from cells of placenta (lanes 1 and 4), 730-3 (lanes 2 and 5) and DU.528 (lanes 3 and 6), and was digested with BamHI (lanes 1-3) or HindIII (lanes 4-6). Panels B-D shows restriction maps of regions surrounding the 1p+ chromosomal breakpoint in DU.528. Panel B shows the normal configuration of the TCR delta locus on chromosome 14. Panel C shows the rearranged TCL-5 locus on the 1p+ chromosome. Panel D shows the complementary germline TCL-5 locus on chromosome 1. Black bars indicate chromosome 14 DNA sequences; white bars indicate chromosome 1 sequences. Probes are shown as hatched boxes. Abbreviations used are: E, EcoRI; B, BamHI; H, HindIII.

FIG. 3 shows that sequences juxtaposed to the TCR delta locus in the translocation chromosome of t(1;14) map to chromosome 1. DNA (10 ug/lane) from the following sources was digested with an excess of restriction enzyme Hind III, electrophoresed, transferred to a nitrocellulose filter, and hybridized with the p528H5.1 probe (see FIG. 2): mouse LMTK$^-$ cell line (lane 1); M44c12S5 hybrid retaining the 14q+ chromosome from the translocation t(8;14)(q24;q32) (lane 2); GL5 hybrid retaining chromosome 4, 13, 14, 18, 20, 21, X and partial chromosomes 17 and 22 (lane 3); 401AD-5EF3 hybrid retaining partial 8 and 22 and chromosomes 19, 21, and X (lane 4); 52-63c17-17 hybrid retaining the 14q+ chromosome from the translocation t(14;X)(q32;q13) (lane 5); GM7299 hybrid retaining chromosomes 1, 6 and X (lane 6); human placenta (lane 7); PB5 hybrid retaining partial chromosomes 1, 2, 3, 5 and 17 (lane 8).

FIG. 6 shows the expression of a TCL-5 transcript in various T-cell lines and a B cell line. Samples (10 ug) of total cellular RNA from five cell lines were electrophoresed in 1% agarose containing 2.2M formaldehyde and then transferred to nitrocellulose. Duplicate filters were prepared and hybridized with the TCL-5 528B0.7 probe (panel A) or with the human ribosomal pA probe (Erickson et al., (1981) Gene 16:1–9) (panel B). Filters were washed with 15 mM NaCl/1 mM sodium phosphate, pH 7.4/0.1 mM EDTA/0.1% NaDodSO$_4$ at 42° C. prior to autoradiography. Lane 1, 730-3; lane 2, TALL-101 (Valtieri et al., (1987) J. Immunol. 138:4042–4050); lane 3, Peer (Hata et al., (1987) Science 238:678–681); lane 4, Jurkat (Sangster et al., (1986) J. Exp. Med. 163:1491–1508); lane 5, 697 (Findley, Jr. et al., (1982) Blood 60:1305–1309).

DETAILED DESCRIPTION

It is a discovery of the present invention that there is an oncogene on chromosome 1 band p32 which is rearranged in the course of the neoplastic process. It is a further finding that the rearrangement leads to increased production of expression products of the oncogene. The oncogene is called TCL-5.

Using nucleic acid sequences of the TCL-5 oncogene, which are provided by the present invention, neoplasms can be diagnosed, assessed or monitored. For example, nucleic acid probes comprising portions of the TCL-5 gene can be used to hybridize to DNA isolated from cells suspected of being neoplastic. The DNA can be digested with restriction endonucleases to form discrete fragments. Detection of hybridized fragments in the isolated DNA of different sizes than those detected by the probe with control DNA samples indicates a TCL-5 rearrangement and neoplasia. The rearrangement may be associated with a t(1;14)(p32;q11) translocation, although other rearrangements are possible which would be detected by the methods of the present invention, such as deletions, insertions and inversions.

The diagnosis of neoplasms generally provides a positive determination that a malignant state exists. Further, by determining that a TCL-5 rearrangement has occurred a classification of the neoplasm can be made to a class of neoplasms involving such rearrangements. The members of a class of neoplasms may respond similarly to therapies, which is useful for choosing a course of treatment.

A neoplasm may be assessed or monitored using the methods of the present invention. This generally provides a quantitative measure of the amount of neoplastic cells remaining in a patient. For example, during the course of anti-neoplastic therapy, e.g., chemotherapy or radiation therapy, the method of the present invention can be used to monitor the success of such therapy. This may involve quantitating the amount of rearranged TCL-5 genes detectable as compared to before therapy. Alternatively, this could involve quantitating the amount and type of TCL-5 gene products and comparing these with levels before therapy.

In another application of the methods of the present invention, TCL-5 rearrangements are determined in a human whose neoplasm has been in remission. If any TCL-5 rearrangements are detected, they provide a measure or indication of minimal residual disease, i.e. the recurrence of detectable neoplastic cells. An indication of minimal residual disease provides the clinician with notice to resume anti-neoplastic therapy.

According to the present invention, DNA of a human is isolated from cells which are suspected of being neoplastic. Such a suspicion may be based on morphological, cytological, or other means relied on by clinicians. It is then determined whether the DNA isolated from the cells contains rearranged TCL-5 genes. While rearrangements involving t(1;14)(p32;q11) translocations are specifically contemplated, other rearrangements involving TCL-5 could occur, such as insertions, deletions or inversions, which would lead to the neoplastic state.

TCL-5 rearrangements have been found to occur in both leukemia and melanoma cells. However, it is not beyond the scope of the invention that other neoplasms would be associated with TCL-5 rearrangements. For example, neuroblastomas may be associated with TCL-5 rearrangements, as chromosome 1 band p32 has been shown to be rearranged in neuroblastoma cells. It is possible that a TCL-5 rearrangement is one of a number of genetic changes that occur during, and contribute to the oncogenic process. If the human is suspected of having leukemia, then T-lymphocytes are the preferred cell source for isolating DNA. If the human is suspected of having melanoma, then melanocytes are the preferred cell source for isolating DNA. However, it is possible that in some cases a TCL-5 rearrangement may be inherited, in which case all somatic cells would carry the rearrangement. People carrying such inherited rearrangements may be prone to develop neoplasms.

According to one method of the present invention a TCL-5 rearrangement is determined by hybridizing a nucleic acid probe derived from chromosome 1 sequences. The probe sequences are those retained on the 1p+ chromosome after a t(1;14)(p32;q11) translocation. The sequences are close enough to the translocation junction (where chromosome 1 sequences are joined to chromosome 14 sequences) that they lie between the translocation junction and a first restriction enzyme site; there are no other sites for the restriction enzyme between the translocation junction and the first site. Such probes hybridize to the TCL-5 RNA transcripts (expression products) and thus can be used to detect and quantify transcripts. Suitable probes are shown in FIG. 2 and include p528B4.4, p528H5.1 and p528B0.7. Probes p528B4.4, p528H5.1 and p528B0.7, have been deposited at the American Type Culture Collection (ATCC) in Rockville, Md., as accession nos. 40627, 40626, and 40625. Preferred probes are those whose sequences lie between the translocation junction and the first EcoRI site. These include those probes named above.

In another method of the present invention the step of determining is performed by amplification of particular sequences by the polymerase chain reaction technique, as is well known in the art. See, Mullis, Science, (1988), vol. 239, pp. 487–491; Scharf, Science, (1988), vol. 233, pp. 1076–1078. The sequences preferably amplified are those which include the translocation junction of a 1p+ chromosome resulting from a t(1;14)(p32;q11) chromosome. Preferably the primers for such amplification are single stranded nucleic acids, one of which comprises chromosome 14 sequences and one of which comprises chromosome 1 sequences. Both sets of sequences are retained on the 1p+ chromosome. The chromosome 14 sequences are preferably derived from the TCR-delta locus encoding the T cell antigen receptor. Most preferably these comprise sequences derived from D-delta-2 or J-delta-1 segments of the locus. A suitable probe of this kind has been deposited at the ATCC as accession no. 67996, and is known as p101J-delta-E5.0. Preferred chromosome 1 primers are derived from sequences on probe p528B0.7, which is adjacent to the translocation breakpoint on chromosome 1.

As mentioned above, gene expression products, including both proteins and ribonucleic acids, in cells suspected of being neoplastic can be quantified and compared to the amount found in control cells. Control cells are isolated from healthy cells of the same human supplying the test cells or from a healthy human. Placental cells may also be used. Methods of quantifying protein and nucleic acids are well known in the art. For example, radiolabeled nucleic acid probes can be used and the amount hybridizing can be determined by autoradiography and densitometry. Other means of quantifying may also be used. Gene products which have been detected in cells carrying t(1;14)(p32;q11) translocations are about 5.4 kb, about 2.2 kb, and about 2.6 kb RNA transcripts. In cells carrying the translocation, the two smaller transcripts are much more abundant than the larger transcript. In cells without the translocation only the larger transcript is detected. The protein products of these transcripts can be detected by antibodies which recognize epitopes on the proteins. Antibodies recognizing epitopes unique to specific protein products can be used to distinguish the populations of TCL-5 proteins. Methods for quantitating protein products are known in the art and may be used as are convenient. One convenient method is the ELISA technique, which employs a colorimetric assay wherein the color correlates with the amount of antigen present. Means of obtaining antibodies for specific protein products are also routine and well known in the art.

Nucleic acid probes and primers discussed above which can be used in the practice of the method of the present invention are also provided. They can be isolated from biological sources such as the deposited cell lines or plasmids mentioned above, or they can be synthesized according to known sequences, for example those shown in FIG. 5. Methods for preparing and labeling probes are well known in the art. Methods for preparing primers are also well known.

The following examples do not limit the scope of the invention, which is described by the preceding description of the invention and the claims appended below.

EXAMPLES

EXAMPLE 1

This example describes the identification of the t(1;14)(p32;q11) chromosomal breakpoint in leukemic cells.

Figure 1:
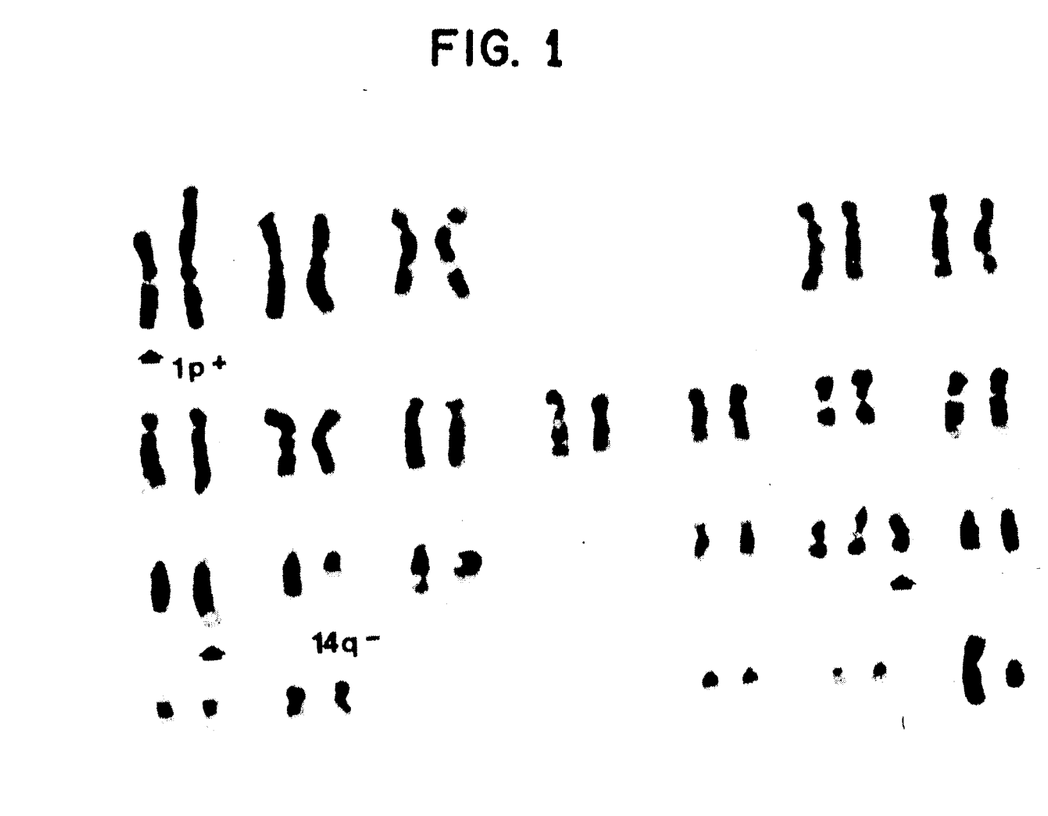
FIG. 1 shows a representative trypsin-Giemsa banded karyotype of the 730-3 cell line: 47, XY, +17, t(1;13)(p32;q34), t(1;14)(p32;q11). The 1p+ and 14q- chromosomes resulting from the t(1;14) translocation involving TCL-5 are designated; the other abnormalities are indicated by arrows.

The t(1;14) chromosomal translocation has been described in the leukemic cells of a 16 year-old boy with acute T lymphoblastic leukemia (Hershfield et al., (1984) Proc. Natl. Acad. Sci. USA 81:253–257). Two cell lines, DU.528 (Kurtzberg et al., (1985) J. Exp. Med. 162:1561–1578) and 730-3 (Kurtzberg, unpublished results), derived from the leukemic cells prior to and after chemotherapy, respectively, showed an apparently identical karyotype. Our description of the 730-3 karyotype is 47, XY, +17, t(1;13)(p32;q34), t(1;14)(p32;q11) (See FIG. 1). This interpretation, with translocations involving the p32 region of both number 1 chromosomes, differs somewhat from the initial report (Kurtzberg et al., (1985) J. Exp. Med. 162:1561–1578).

Figure 2A:
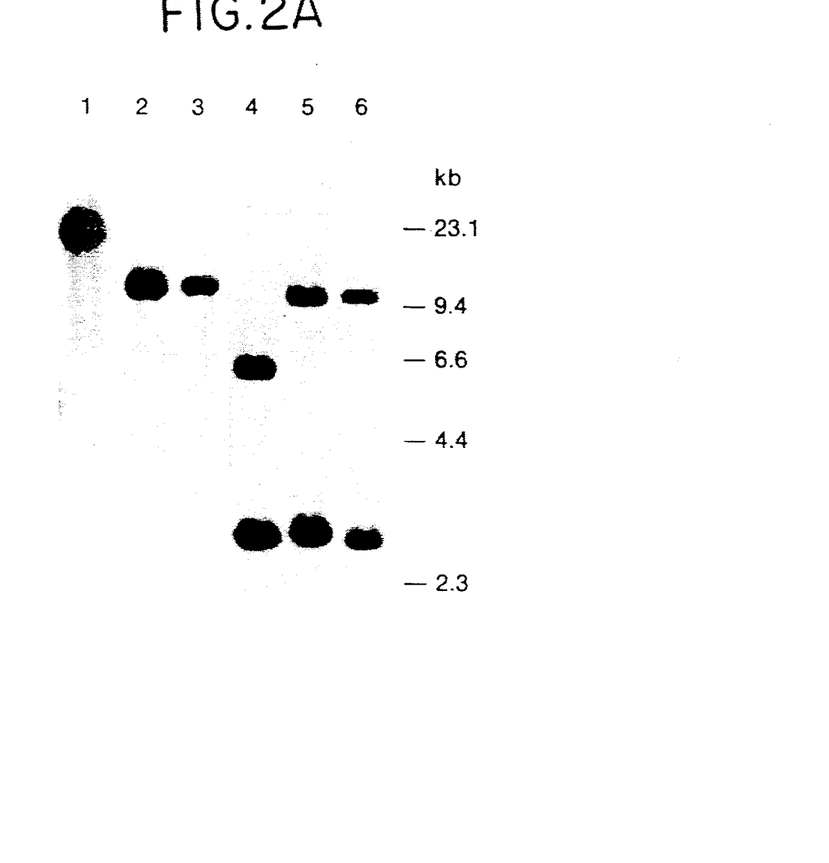
Figure 2B:
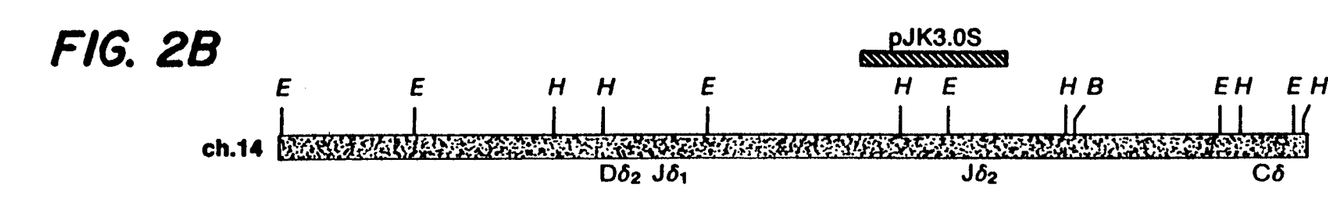

On chromosome 14 at band q11 the T-cell receptor (TCR) constant delta chain gene lies within the TCR alpha locus approximately 85 kb upstream of the constant alpha locus region (Isobe et al., (1988) Proc. Natl. Acad. Sci. USA 85:3933–3937); Takihara et al., (1988) Proc. Natl. Acad. Sci. USA 85:6097–6101). Direct involvement of the TCR delta locus in the t(1;14) translocation was suggested by the results of the hybridization of the TCR delta pJK3.0S probe to a Southern filter with bound DU.528 and 730-3 DNAs (FIG. 2A). This probe, which contains a 3.0 kb SstI fragment located within the TCR delta locus as illustrated in FIG. 2B, hybridizes to a 10.5 kb BamHI rearranged fragment in both DU.528 and 730-3 Bam HI-digested DNAs (FIG. 2A, lanes 2,3). Since the pJK3.0S insert has an internal HindIII site, the probe detects two germline restriction fragments of 3.4 kb and 6.2 kb in HindIII-digested placental DNA (FIG. 2A, lane 4). In contrast to the expected germline HindIII pattern, pJK3.0S detects a 3.4 kb germline restriction fragment and a 9.8 kb rearranged restriction fragment in HindIII-digested DNAs of DU.528 and 730-3 cells (FIG. 2A). Thus, we concluded that the t(1;14) breakpoint probably occurred within the 9.8 kb HindIII fragment detected by the pJK3.0S probe (FIG. 2A). The lack of pJK3.0S hybridization to both a 19 kb BamHI germline fragment and a 6.2 kb HindIII germline fragment originating from the DU.528 (and 730-3) non-translocated chromosome 14 may be due to the deletion of this delta allele following functions V alpha-J alpha rearrangement.

Figure 2C:
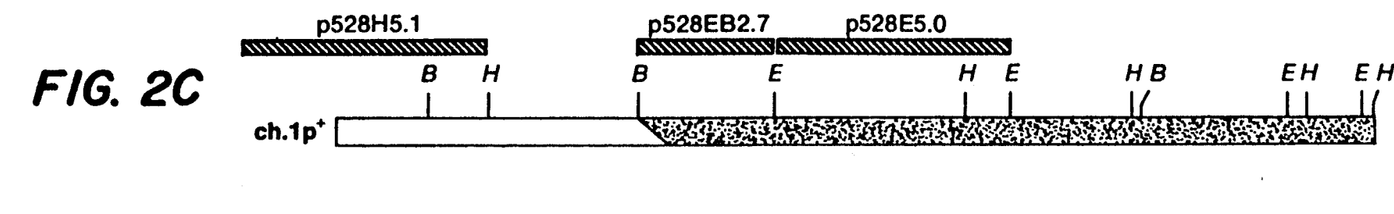
Figure 2D:
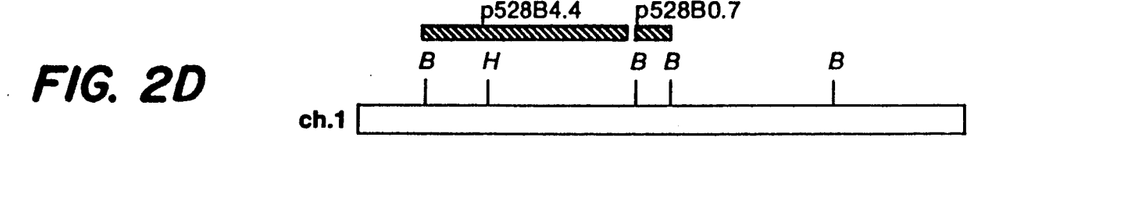
Figure 3:
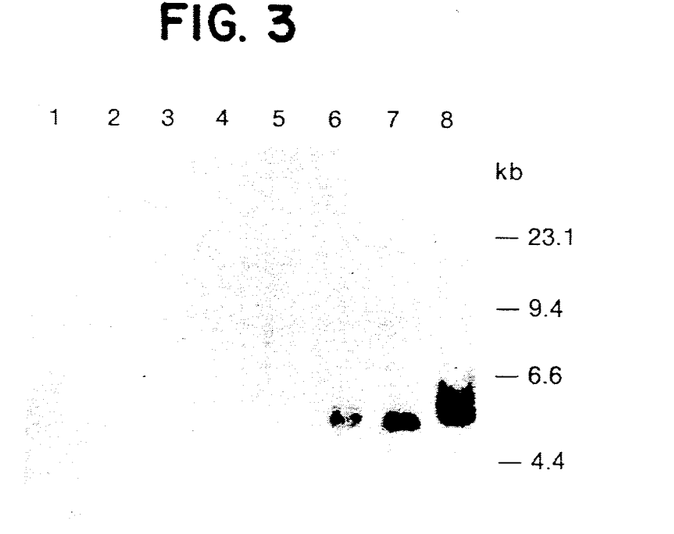

We have cloned the t(1;14) chromosomal breakpoint from a DU.528 genomic library constructed in the lambda phage vector EMBL3A (Fishauf et al., (1983) J. Mol. Biol. 170:827-842). One class of rearranged clones from the phage library of DU.528 was obtained and a representative map of the overlapping phage clones is shown in FIG. 2C. The size of the rearranged DU.528 fragments (FIG. 2A) are in agreement with the calculated values for the appropriate restriction fragments in the rearranged clone (FIG. 2C). In order to determine the point of divergence from the TCR delta sequences in the rearranged clone, the chromosome 14 p528E5.0 probe, containing a 5.0 kb EcoRI fragment as illustrated in FIG. 2B, was used to isolate and map the complementary germline TCR delta locus from a human placental library (FIG. 2B). A repeat-free 5.1 kb HindIII fragment located close to the breakpoint, where the restriction enzyme sites had diverged from the normal delta locus restriction sites (FIG. 2C), was cloned into pUC19 (p528H5.1) to be used in determining its chromosomal origin. Probe p528H5.1 was hybridized to a Southern filter with bound DNA from rodent×human hybrid cells containing either human chromosome 1 or human chromosome 14. The presence in the hybrids of the 5.1 kb HindIII fragment correlates only with the presence of human chromosome 1 (FIG. 3), demonstrating that we have cloned the t(1;14) breakpoint on the DU.528 1p+ chromosome (1qter->1p32::14q11->14qter). The p528H5.1 probe was also used to screen a human placental library in order to clone the normal chromosome 1 counterpart of the breakpoint region (FIG. 2D).

Procedures for molecular cloning, Southern blot analysis, RNA isolation and Northern blot analysis were performed as described previously (Finger et al., (1988) Proc. Natl. Acad. Sci USA, 85:9158-9162).

The various probes cloned in this study contain inserts ligated in pUC19. The details of each probe are described in the text and are illustrated in figures when relevant. All probes were radiolabeled by nick translation using alpha-$^{32}$P dNTPs to a specific activity of approximately $5 \times 10^8$ cpm/ug.

Isolation, propagation and characterization of parental cells and somatic cell hybrids used in this study have been described elsewhere (Croce et al., 1985, Blood 65:1-7); Durst et al., 1987, Proc. Natl. Acad. Sci. USA 84:1070-1074); Haluska et al., 1988, Proc. Natl. Acad. Sci. USA 85:2215-2218). The presence of specific human chromosomes or regions of chromosomes has been confirmed by DNA hybridization using probes for genes assigned to specific human chromosome regions. GM7299 is a somatic cell hybrid obtained from the NIGMS Human Genetic Mutant cell repository (Camden, N.J.).

EXAMPLE 2

This example demonstrates the isolation of the reciprocal translocation joining segment.

Figure 4A:
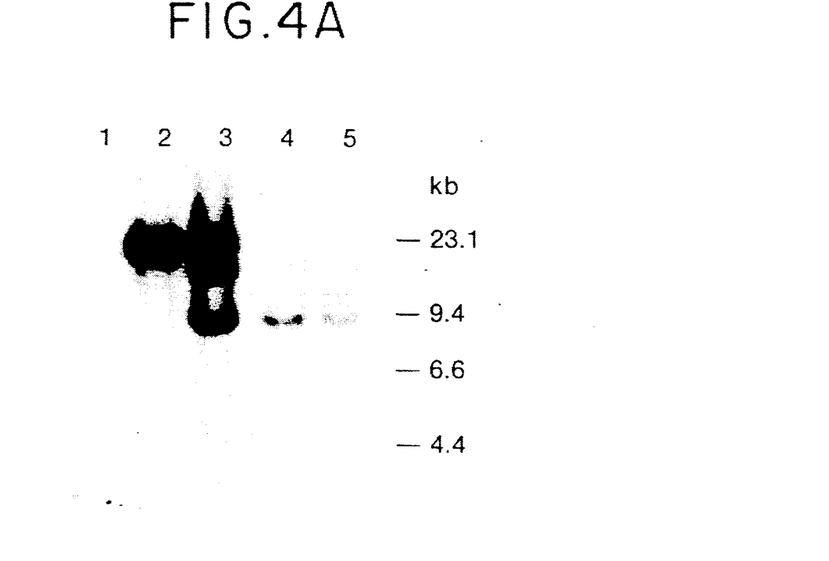
FIG. 4 depicts the 14q$^-$ chromosomal reciprocal breakpoint. Panel A shows a Southern filter hybridized with the p528B0.7 probe (see FIG. 2) containing a germline chromosome 1 insert encompassing the t(1;14) breakpoint. DNA (10 ug/lane) from mouse cell line (lane 1), human placenta (lane 2), DU.528 cell line (lane 3), hybrid 726c122 (lane 4) and hybrid 726c124 (lane 5) was digested with EcoRI, electrophoresed, and transferred to a nitrocellulose filter. Panel B shows restriction maps of the chromosome 14 TCR delta locus (black bar) and the chromosome 1 TCL-5 locus (white bar) that recombined to form the 14q$^-$ chromosome of the t(1;14) translocation (black and white bar). E, EcoRI; B, BamHI; H, HindIII.

To complete analysis of the structural aspects of the t(1:14) translocation, we wanted to analyze the joining segment between chromosomes 1 and 14 on the derivative 14q$^-$ chromosome (14pter->14q11::1p32->1pter). The p528B0.7 probe contains a germline 0.7 kb BamHI insert from chromosome 1 that includes the DU.528 1p+ translocation breakpoint (as illustrated in FIG. 2D). Upon hybridization with the p528B0.7 probe, an EcoRI digest of DU.528 DNA showed a germline fragment of 17.5 kb and rearranged fragments of 8 kb and 14 kb (FIG. 4A, lane 3). The 17.5 kb EcoRI fragment (FIG. 4A, lanes 2,3) corresponds to the germline chromosome 1 fragment detected in both the DU.528 and human control DNAs. The 14 kb EcoRI rearranged fragment (FIG. 4A, lane 3) corresponds to the EcoRI segment encompassing the breakpoint on the DU.528 chromosome 1p+, a conclusion based on restriction analysis using the p528EB2.7 probe. The p528EB2.7 probe spans the DU.528 chromosome 1p+ breakpoint, as depicted in FIG. 2C, and detects the same size 14 kb rearranged fragment in DU.528 EcoRI-digested DNA.

Figure 4B:
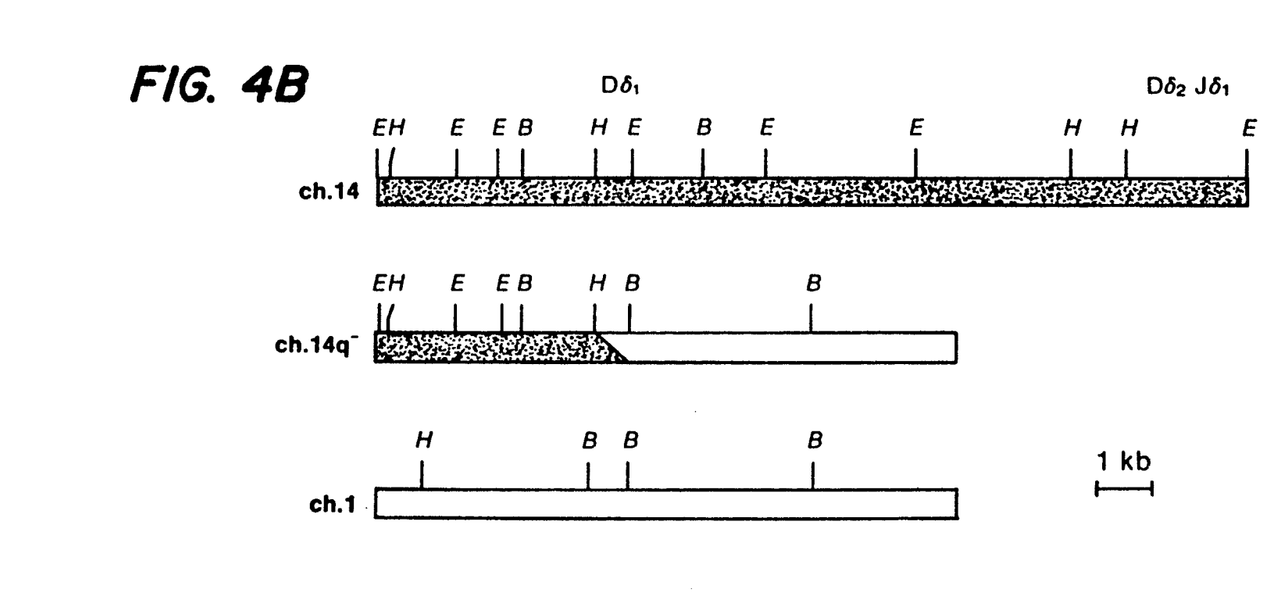

The 8 kb EcoRI rearranged fragment (FIG. 4A, lane 3) could correspond to the translocation junction on the derivative chromosome 14q$^-$ in DU.528. We therefore rescreened the DU.528 genomic library with the p528B0.7 probe, our objective being to obtain clones corresponding to the 14q+ chromosome. After the initial library screening, phage clones that hybridized to the p528B0.7 probe but not to the p528EB2.7 probe (a probe that hybridizes to DU.528 phage clones with inserts covering the chromosome 1p+ junction or the normal chromosome 1 counterpart) were isolated and characterized in detail. The rationale for the differential screening process was to isolate only the clones potentially containing the translocation junction on the reciprocal 14q$^-$ chromosome. A comparison of the restriction map representing the above isolated clones with the restriction maps representing the chromosome 1 and chromosome 14 normal counterparts presented in FIG. 4B clearly demonstrates that we have also cloned the chromosome 14q$^-$ reciprocal breakpoint of the t(1;14) translocation in DU.528.

By subcloning mouse-human hybrids isolated after fusion of mouse and 730-3 cells, we obtained hybrid lines 726c122 and 726c124 which retained the 8 kb EcoRI rearranged fragment corresponding to the 14q$^-$ (14pter->14q11::1p32>1pter) chromosomal junction region (FIG. 4A, lanes 4,5). The two hybrids also retained the L-MYC locus which has been mapped to chromosome region 1p32 (Nau et al., 1985, Nature 318:69-73) but did not retain the nerve growth factor beta locus assigned to chromosome region 1p22 or 1p13 (Munke et al., 1984, Somat. Cell. Genet. 10:589-599); Garson et al., 1987, Nucl. Acids Res. 15:4761-4770). Thus, analysis of the somatic cell hybrids is consistent with the TCL-5 locus residing on the short arm of chromosome 1 centromeric to the L-MYC locus and telomeric to the nerve growth factor beta locus.

EXAMPLE 3

This example shows that the chromosome 14 sequences involved in the t(1;14)(p32;q11) translocation are in the D-delta locus. The nucleotide sequence of the translocation junction is also shown.

After fine genomic mapping of regions of interest, DNA fragments were subcloned in M13mp18 or M13mp19 and their sequences were determined by using the Sanger dideoxy method (Sanger et al., 1977. Proc. Natl. Acad. Sci USA 74:5463–5467) with Sequenase (United States Biochemical, Cleveland).

Figure 5A:
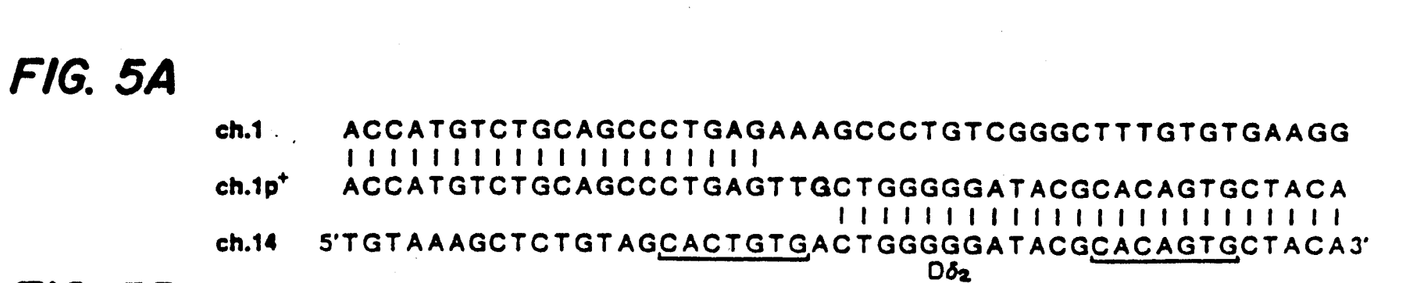
FIG. 5 compares the nucleotide sequence at the t(1;14) translocation junctions and the corresponding germline sequences. Panel A shows the 1p+ chromosome breakpoint sequence. Panel B shows the 14q$^-$ chromosomal reciprocal breakpoint sequence. Germline chromosome 14 D-delta$_1$ and D-delta$_2$ sequences are shown as previously published (Takihra, et al., (1988) Proc. Natl. Acad. Sci. USA 85:6097–6101). Brackets indicate heptamer signal sequences of the D-delta segments. The sequences shaded in gray are thought to represent N regions.

The nucleotide sequences of the translocation junction sites and the normal counterparts are presented in FIG. 5. Except for the loss of one nucleotide at the breakpoint, the chromosome 1 sequences at the junction on the 1p+ chromosome and the 14q− chromosome are continuous in relation to the germline chromosome 1, thus demonstrating the reciprocity of the translocation in relation to chromosome 1. Examination of the sequence from chromosome 14 at the translocation junction identified features which may have influenced the translocation process. The joining on the 1p+ chromosome occurred at the D-delta$_2$ segment (FIG. 5A). An unrearranged D-delta$_2$ segment normally possesses the 3′ and 5′ heptamer and nonamer recombination signal sequences used during D segment rearrangements (Takihara et al., 1988, Proc. Natl. Acad. Sci. USA 85:6097–6101). Strikingly, the t(1;14) breakpoint on the 1p+ chromosome occurred in D-delta$_2$ precisely at a site where normal D segment rearrangement occurs, i.e., at the site immediately 3′ to the 5′ signal sequences, such that these sequences are lost during the recombination process (Sakano et al., 1981, Nature 290:562–565).

Figure 5B:
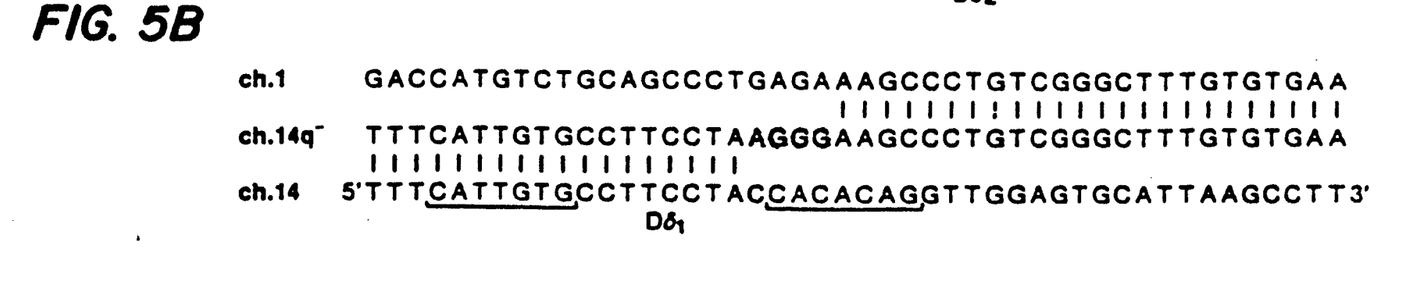

The chromosome 14 sequences from the reciprocal chromosome 14q− side of the breakpoint demonstrate that the junction site is at the D-delta$_1$ segment of the TCR delta locus (FIG. 5B). Analogous to normal D segment rearrangement (Sakano et al., 1981, Nature 290:562–565), the reciprocal breakpoint has occurred precisely 5′ to the 3′ D-delta$_1$ signal sequences. Extra nucleotides present at both the junction sites on chromosomes 1p+ and 14q− are highlighted by the stippled boxes in FIG. 5 and are not derived from the normal germline sequences. Such additional nucleotides at breakpoints in B-and T-cell translocations may represent N regions (Tsujimoto et al., 1985, Science 229:1390–1393; 1985, Nature 315:340–343; Finger et al., 1986, Science 234:982–985; Haluska, et al., 1986, Nature 324:158–161), stretches of extra nucleotides that are presumably added by the enzyme terminal transferase (Desiderio et al., 1984, Nature, 311:752–755) at the pre-B and pre-T cell stage of differentiation. Because of the involvement of the D-delta coding segments and their accompanying recombinational signals, the present results suggest that the recombination process mediating this chromosomal translocation is catalyzed by the same recombinase system that normally carries out the joining of T-cell receptor delta gene segments.

EXAMPLE 4

This example demonstrates that there is a gene located at the translocation junction on chromosome 1.

Frequently, chromosomal loci aberrantly juxtaposed to immunoglobulin super family loci by chromosomal rearrangements are inappropriately transcriptionally active, a feature which is thought to reflect the transcription of a gene contributing directly to the malignant process (reviewed in Finger et al., 1989, "Involvement of the Immunoglobulin Loci in B-cell Neoplasms," in *Immunoglobulin Genes*(F. Alt, T. Honjo and T. H. Rabbitts, eds.) Academic Press, Ltd. London, pp. 221–230). We therefore sought evidence for the presence of a gene located in the region of chromosome 1 adjacent to the t(1;14) translocation breakpoint by performing Northern blot analysis using purified insert from the p528B0.7 probe (528B0.7), a fragment from normal chromosome 1 which overlaps the breakpoint.

Figure 6:
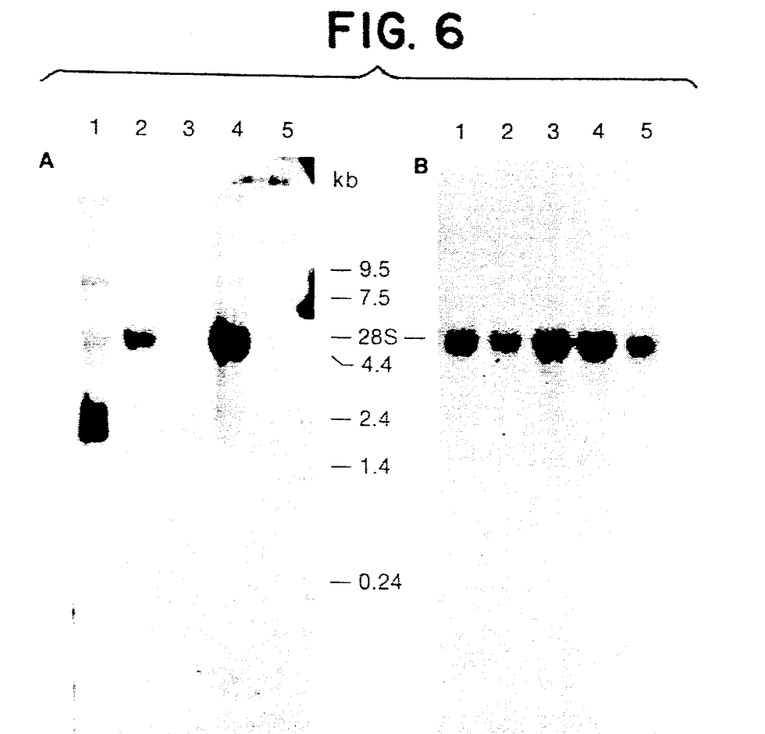

Total cellular RNAs used for Northern blot analyses were from 730-3, a T-cell ALL cell line (TALL-101), a gamma/delta-producing T-cell line (Peer), an alpha/-beta-producing T-cell line (Jurkat), and a pre-B-cell leukemia cell line (697). Hybridization of a filter retaining these RNAs to a ribosomal probe indicates that there are similar amounts of 28S ribosomal RNA in sample lanes (FIG. 6B). The same RNA preparations on a duplicate filter show varying sizes and amounts of transcripts hybridizing to the chromosome 1 probe, 528B0.7 (FIG. 6A). The 528B0.7 probe detects a 5.4 kb RNA transcript and possibly a low level of 2.2 kb and 2.6 kb RNA transcripts in the T-cell lines Jurkat and TALL-101. The gene represented by these transcripts, located at the translocation junction on chromosome 1, is designated TCL-5 (T-cell leukemia/lymphoma-5). A barely detectable level of a 5.4 kb TCL-5 RNA transcript in the 730-3 and Peer T-cell lines and the 697 pre-B cell line may be due to either low level expression of TCL-5 or to nonspecific cross-hybridization to 28S ribosomal RNA. In the 730-3 cell line, however, the 528B0.7 probe detects a high level of expression of the 2.2 kb and 2.6 kb TCL-5 RNA transcripts, suggesting that an alteration of TCL-5 gene expression in 730-3 cells is directly involved in the neoplastic process in this human T-cell leukemia.

EXAMPLE 5

This example demonstrates that the TCL-5 locus is rearranged in a melanoma cell line with a 1p32 chromosomal abnormality.

A number of human cutaneous malignant melanomas (CMM) have been shown to carry non-random chromosome 1p deletions or rearrangements which often appear to involve the proximal segment 1p12- 1p22 (Balaban et al., 1986, Cancer Genet. Cytogenet., 19:113–122). Approximately 8–12% of all CMMs occur in individuals with a family history of the disease (Greene and Fraumeni, 1979, "The Hereditary Variant of Malignant Melanoma," in *Human Malignant Melanoma*, Grune and Stratton, N.Y., pp. 139–166). Genetic studies of familial CMM kindreds indicate a highly penetrant, autosomal, dominant mode of inheritance for a dysplastic nevus syndrome/CMM susceptibility gene with provisional linkage to the Rh blood locus on chromosome region 1p34–36 (Greene et al., 1983, Proc. Natl. Acad. Sci. USA 80:6071–6075).

Figure 7:
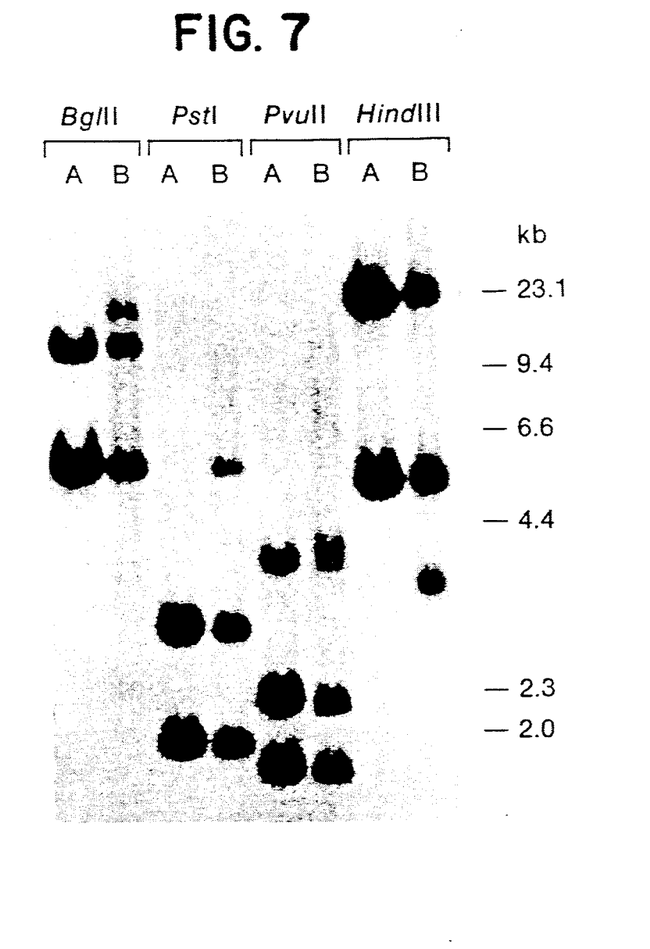
FIG. 7 demonstrates that there is a rearrangement of the TCL-5 locus in WM8 melanoma DNA. 10 ug of GM607 DNA used as a germline control (lanes A) or WM8 DNA (lanes B) were digested with the enzymes indicated, fractionated and hybridized with the p528B4.4 probe.
Figure 8A:
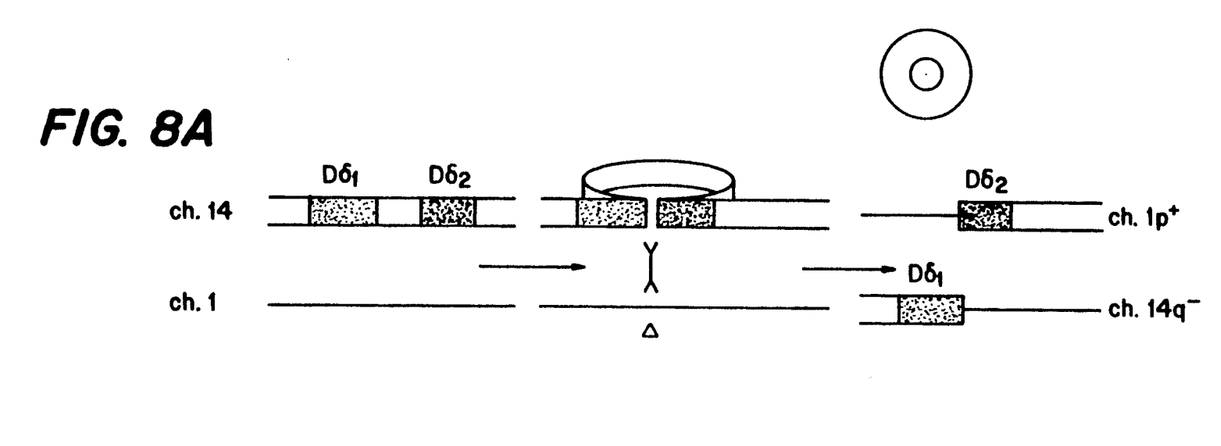
FIG. 8 depicts two models of the t(1;14) translocation event. D delta$_1$ and D delta$_2$ segments are shown by the stippled and filled boxes, respectively. Chromosome 1 and 14 are shown by a single and a double line, respectively. In Panel A the translocation and D delta$_1$-D delta$_2$ attempted joining occur simultaneously. In Panel B the D delta$_1$-D delta$_2$ joining precedes the translocation. The triangle represents the breakpoint site on chromosome 1.
Figure 8B:
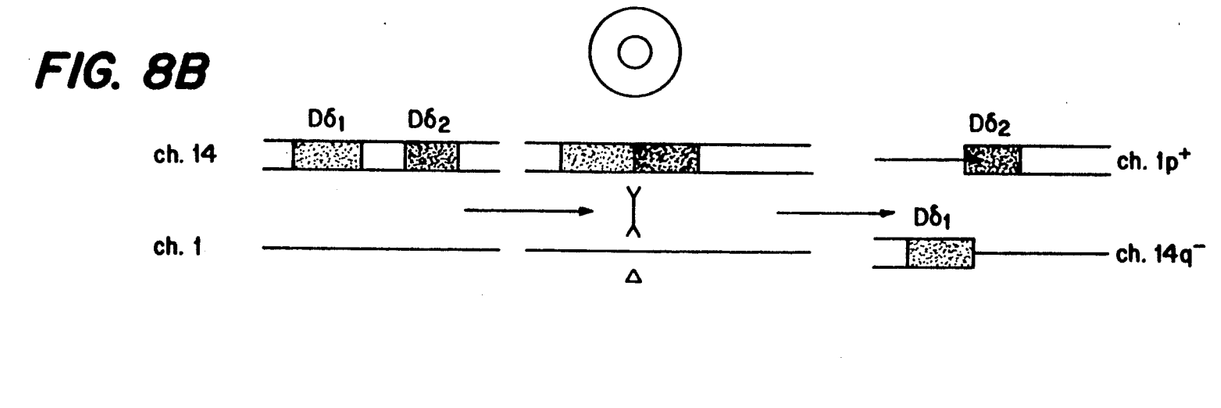

We have examined the possible involvement of the TCL-5 locus in chromosome 1 aberrations in several melanoma cell lines. The p528B4.4 probe, which contains a 4.4 BamHI fragment derived from chromosome 1 adjacent to the breakpoint on the 1p+ chromosome as illustrated in FIG. 2D, detected a genomic rearrangement in DNA from the primary melanoma cell line WM8. Two DNA preparations from the WM8 cell line yielded identical results (FIG. 7, lanes B,C). The WM8 cell line carries a del(1)(p32) and numerous other chromosomal aberrations (M. Herlyn and P. C. Nowell, unpublished results). Genomic rearrangements detected in WM8 DNA compared to human control DNA using several different restriction enzymes allowed us to exclude restriction fragment length polymorphisms as an explanation of the new rearranged fragments. The lower intensity of the rearranged restriction fragments relative to the germline restriction fragments may be due to a low copy number of the del(1)(p32) chromosome relative to the other chromosomes 1 observed in WM8, which is a hypotetraploid cell line.

I claim:

1. A method of diagnosing or assessing a neoplasm in a human comprising:
   isolating DNA of a human from cells suspected of being neoplastic;
   determining whether a TCL-5 gene on said DNA has been rearranged, a rearranged TCL-5 gene indicating a neoplasm.

2. The method of claim 1 wherein the neoplasm is leukemia.

3. The method of claim 1 wherein the neoplasm is melanoma.

4. The method of claim 1 wherein the cells from which DNA is isolated are T-lymphocytes of the human.

5. The method of claim 1 wherein the cells from which DNA is isolated are melanocytes of the human.

6. The method of claim 1 wherein the step of determining is performed by hybridization of a nucleic acid probe derived from chromosome 1 sequences located between a translocation junction of a 1p+ chromosome of a t(1;14)(p32;q11) translocation and a restriction enzyme site, wherein there are no other sites for said enzyme between said site and the translocation junction.

7. The method of claim 6 wherein the probe is derived from sequences between the translocation junction and an Eco RI site.

8. The method of claim 1 wherein the step of determining is performed by amplifying sequences comprising a translocation junction of a 1p+ chromosome of a t(1;14)(p32;q11) translocation.

9. The method of claim 7 wherein the probe is p528B0.7 deposited at the ATCC as accession no. 40625.

10. The method of claim 8 wherein the amplifying is performed using primers comprising chromosome 14 and chromosome 1 sequences.

11. The method of claim 10 wherein the chromosome 14 sequences are derived from D-delta-2 or J-delta-1 segments of the TCR-delta locus.

12. The method of claim 10 wherein the chromosome 1 sequences are derived from sequences on p528B0.7 deposited at the ATCC as accession no. 40625.

13. A method of diagnosing or assessing a neoplasm in a human, comprising:
   isolating from the human test cells suspected of being neoplastic;
   determining the quantity of expression products of TCL-5 genes in said test cells;
   comparing the quantity of TCL-5 gene expression products in said test cells with the quantity in control cells, said control cells isolated from healthy cells of the human or from a healthy human, an altered quantity of TCL-5 gene expression products in said test cells relative to said control cells indicating a neoplasm.

14. The method of claim 13 wherein the gene expression products are RNA transcripts.

15. The method of claim 14 wherein the gene expression products are transcripts of sizes selected from the group consisting of: about 5.4 kb, about 2.2 kb, and about 2.6 kb.

16. An isolated nucleic acid probe consisting essentially of:
   a chromosome 1 restriction fragment, or a portion thereof, said fragment consisting essentially of a translocation junction of a 1p+ chromosome of a t(1;14)(p32;q11) translocation wherein the chromosome 1 nucleotide sequence of said translocation junction is ACCATGTCTGCAGCCCTGAG.

17. The probe of claim 16 wherein the restriction fragment is a 17.5 kb EcoRI fragment.

18. The probe of claim 17 which is p528B0.7 deposited at the ATCC as accession no. 40625.

19. A pair of nucleic acid primers for amplifying translocation junctions of a 1p+ chromosome of a t(1;14)(p32;q11) translocation as shown in FIG. 5, wherein one primer of the pair consists essentially of chromosome 1 sequences of said 1p+ chromosome and one primer consists essentially of chromosome 14 sequences of said 1p+ chromosome, wherein said pair of primers directs the amplification of a translocation junction of a t(1;14)(p32;q11) translocation.

20. The primer pair of claim 19 wherein the chromosome 14 sequences are derived from D-delta-2 or J-delta-1 segments of the TCR-delta locus.

21. The primer pair of claim 19 wherein the chromosome 1 sequences are derived from sequences on p528B0.7 deposited at the ATCC as accession no. 40625.

22. The method of claim 1 wherein the human has received anti-neoplastic therapy and detection of a rearranged TCL-5 gene is a measure of efficacy of the therapy.

23. The method of claim 1 wherein the neoplasm in the human has been in remission and detection of a rearranged TCL-5 gene is a measure of minimal residual disease.

24. The probe of claim 16 wherein said fragment consists essentially of sequences of p528B0.7, deposited at ATCC as accession no. 40625.

25. The probe of claim 16 wherein said fragment consists essentially of sequences of p528B4.4, deposited at ATCC as accession no. 40627.

26. The probe of claim 16 wherein said fragment consists essentially of sequences of p528H5.1, deposited at ATCC as accession no. 40626.

27. The primer pair of claim 19 wherein the chromosome 1 sequences consist essentially of sequences of p528B4.4, deposited at ATCC as accession no. 40627.

28. The primer pair of claim 19 wherein the chromosome 1 sequences consist essentially of sequences of p528H5.1, deposited at ATCC accession no. 40626.

* * * * *

UNITED STATES PATENT AND TRADEMARK OFFICE
CERTIFICATE OF CORRECTION

PATENT NO.　：　5,242,795
DATED　　　：　September 7, 1993
INVENTOR(S)：　Carlo M. Croce

It is certified that error appears in the above-identified patent and that said Letters Patent is hereby corrected as shown below:

On the title page, items [19] and [75]:
In line 2, please delete the name "Croco" and insert -- Croce --.

In line 6, item [75], delete "Carle M. Croco" and insert -- Carlo M. Croce --.

Signed and Sealed this

Fifteenth Day of March, 1994

*Attest:*

BRUCE LEHMAN

*Attesting Officer*　　　*Commissioner of Patents and Trademarks*